United States Patent [19]

Wasley

[11] Patent Number: 4,897,399
[45] Date of Patent: Jan. 30, 1990

[54] HETEROTERTRACYCLIC LACTAM DERIVATIVES, PHARMACEUTICAL COMPOSITIONS, AND METHOD OF TREATING IMPAIRED MEMORY AND LEARNING

[75] Inventor: Jan W. F. Wasley, Chatham, N.J.

[73] Assignee: Ciba-Geigy Corp., Ardsley, N.Y.

[21] Appl. No.: 183,802

[22] Filed: Apr. 20, 1988

[51] Int. Cl.[4] .................... A61K 31/435; C07D 471/02
[52] U.S. Cl. ........................................ 514/288; 546/66
[58] Field of Search ........................... 546/66; 514/288

[56] References Cited

FOREIGN PATENT DOCUMENTS 0100786 8/1981 Japan .
0110686 9/1981 Japan .

OTHER PUBLICATIONS

Monden et al., "Über die Kondensation der Cyclohex.", Chem. Ber. 92: pp. 2552–2555 (1959).
Mondon, "Eine Neue Vorstofe zum Arfbon von Erythrmancu", Chem. Ber. 92, pp. 1472–1477 (1959).
Bergmann et al., "Studies in Chem. of Eryth. Alka. Deriv.", Tetrahedron 32: pp. 2847–2852 (1976).
Tsuda et al., "Pract. Rte. to Spiro-Type Hetero.", Heterocycles, vol. 15, No. 1, pp. 431–436 (1981).
Chem. Abst. 96:104577s of Japanese 81/108 789 (1982).
Chem. Abstr. 96:104578t of Japanese 81/110 686 (1982).
Chem. Abstr. 96:104579u of Japanese 81/113 784 (1982).
Chem. Abstr. 96:104580n of Japanese 81/113 785 (1982).
Derwent Abstract 76494D of Japanese 110 686 (1981).
Dewent Abstract 74741D of Japanese 108 789 (1981).
Chem. Ber., vol. 92, pp. 2552–2555 (1959).
Tetrahedron, vol. 32, No. 21, pp. 2617–2620 (1976).
Tetrahedron, vol. 32, pp. 2847–2852 (1976).
Heterocycles, vol. 15, No. 1, pp. 431–436 (1981).
Liebig's Annalen, vol. 628, pp. 123–143 (1959).
Chem. Ber., vol. 92, pp. 1461–1477 (1959).
Chem. Pharm. Bull., vol. 8, pp 290–293 (1960).
Tetrahedron Letters, No. 14, pp. 5–8 (1960).
Synthesis, pp. 119–120 (1981).

*Primary Examiner*—Mukund J. Shah
*Assistant Examiner*—Andrew G. Rozycki
*Attorney, Agent, or Firm*—Norbert Gruenfeld

[57] ABSTRACT

Disclosed are the compounds of formula I:

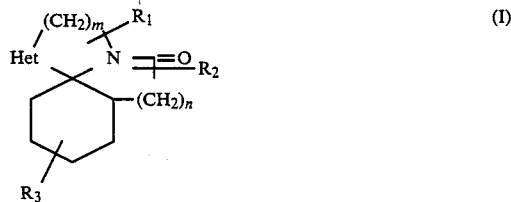

wherein $R_1$–$R_3$ represent hydrogen or lower alkyl; m represents the integer 2 or 3; n represents the integer 1 or 2; Het represents a pyrrole or imidazole ring bonded at any two adjacent positions and optionally substituted by one or two or lower alkyl; and pharmaceutically acceptable salts of compounds of formula I wherein Het represents optionally substituted imidazole; their methods of preparation; pharmaceutical compositions thereof, and their use for treating cognitive disorders in mammals.

9 Claims, No Drawings

HETEROTERTRACYCLIC LACTAM DERIVATIVES, PHARMACEUTICAL COMPOSITIONS, AND METHOD OF TREATING IMPAIRED MEMORY AND LEARNING

SUMMARY OF THE INVENTION

The invention relates to the optionally substituted tetracyclic compounds of the general formula I as defined herein, which are useful in the prevention and treatment of cognitive dysfunction in mammals, processes for preparing same, pharmaceutical compositions comprising said compounds, and methods of treating conditions and syndromes in mammals responsive to improvement of cognitive performance by administration of said compounds to mammals in need thereof.

The compounds of this invention improve cognitive performance including memory and learning in mammals and can be used for the treatment of cognitive impairment, e.g. impairment of memory and learning, in mammals which occurs e.g. in conditions of amnesia, dementia (such as Alzheimer's disease or senile dementia), dyslexia, transient cerebral ischemia and the like.

DETAILED DESCRIPTION OF THE INVENTION

Particularly the invention is directed to the compounds of formula I

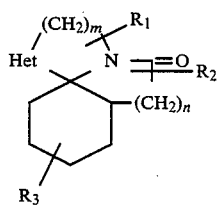

wherein $R_1$–$R_3$ represent hydrogen or lower alkyl; m represents the integer 2 or 3; n represents the integer 1 or 2; Het represents a pyrrole or imidazole ring bonded at any two adjacent positions and optionally substituted by one or two of lower alkyl; and pharmaceutically acceptable salts of compounds of formula I wherein Het represents optionally substituted imidazole.

Particular embodiments of the invention relate to said compounds wherein, in formula I, m represents the integer 2 and n represents the integer 1 or 2; compounds wherein, in formula I, m represents the integer 3 and n represents the integer 1 or 2; further to said compounds wherein, in formula I, m represents the integer 2 or 3 and n represents the integer 1; also to said compounds wherein, in formula I, m represents the integer 2 or 3 and n represents the integer 2.

Preferred are said compounds wherein, in formula I, m represents the integer 2 and n represents the integer 1.

In the compounds of the invention of formula I the ring junction between the cyclohexane and lactam rings may be either cis or trans fused. Furthermore, the compounds of the invention can also exist in the form of optically active isomers. The resulting racemic and optically active isomers are within the purview of the invention.

Specific embodiments of the invention relate to the above-cited compounds wherein, in formula I, Het represents pyrrole optionally substituted by lower alkyl and further to the above-cited compounds wherein, in formula I, Het represents imidazole optionally substituted by lower alkyl.

When Het represents the imidazole ring, the two points of attachment in formula I, can be to the adjacent 1 and 2 or adjacent 4 and 5 positions of the imidazole ring.

When Het represents the pyrrole ring, the two points of attachment in formula I can be to the adjacent 1 and 2, adjacent 2 and 3 or adjacent 4 and 5 positions of the pyrrole ring.

Preferred are the above-cited compounds of formula I wherein $R_1$, $R_2$ and $R_3$ independently represent hydrogen or lower alkyl; Het represents

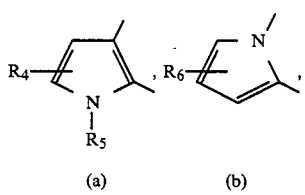

(a) (b)

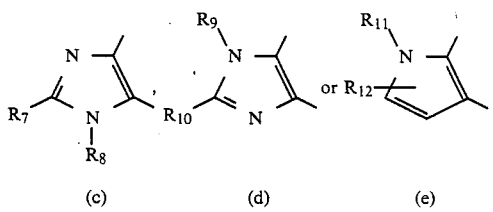

(c) (d) (e)

wherein $R_4$–$R_{12}$ independently represent hydrogen or lower alkyl; and pharmaceutically acceptable acid addition salts of compounds wherein Het represent (c) or (d).

Further preferred are the compounds of the formula II

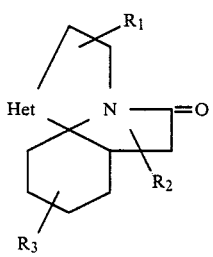

where in $R_1$, $R_2$ and $R_3$ independently represent hydrogen or lower alkyl; Het represents

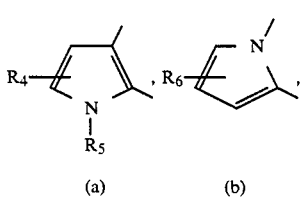

(a) (b)

-continued

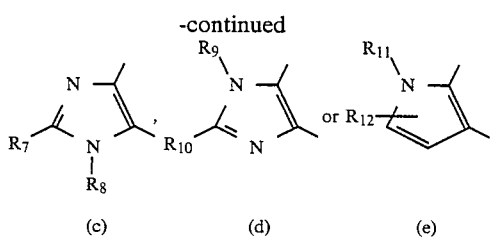

(c)   (d)   (e)

wherein $R_4$–$R_{12}$ independently represent hydrogen or lower alkyl; and pharmaceutically acceptable acid addition salts of compounds wherein Het represents (c) or (d).

Preferred in turn are said compounds of the formula II and particular embodiments thereof wherein the cyclohexane and pyrrolidone rings are cis fused, as represented by formula IIa

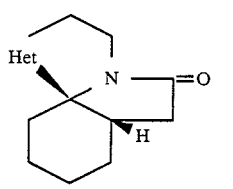
(IIa)

and wherein Het has meaning as defined herein.

Particular embodiments, of the invention in turn relate to the cited compounds of formula I, II, and IIa wherein Het represents rings (a) or (e), (c) or (d), or (b), respectively as defined above.

Particularly preferred are the octahydro-2H-pyrrolo-[2',1':3,4]pyrazino[2,1-i]indol-2-ones of formula III

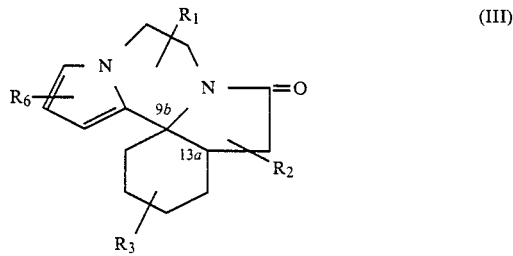
(III)

wherein $R_1$, $R_2$, $R_3$ and $R_6$ represent hydrogen or lower alkyl.

A preferred embodiment thereof relates to the compounds of formula III wherein $R_1$, $R_2$, $R_3$ and $R_6$ represent hydrogen; and further to above-cited compounds of formula III wherein the cyclohexane and pyrrolidone rings are cis fused.

Also preferred are the octahydro-2H-pyrrolo[2',3':3,4]-pyrido[2,1-i]indol-2-one derivatives of formula IV

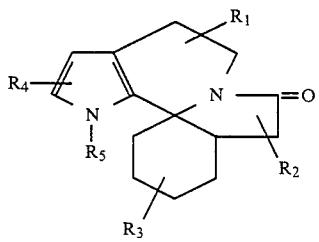
(IV)

wherein $R_1$–$R_5$ represent hydrogen or lower alkyl.

Preferred embodiments thereof relate to the compounds of formula IV wherein $R_1$–$R_4$ represent hydrogen and $R_5$ represents hydrogen or lower alkyl; and further to above cited compounds of formula IV wherein the cyclohexane and pyrrolidone rings are cis fused.

A further preferred embodiment of the invention relates to the octahydro-2H-pyrrolo[3',2':3,4]-indol-2-ones of the formula IVa

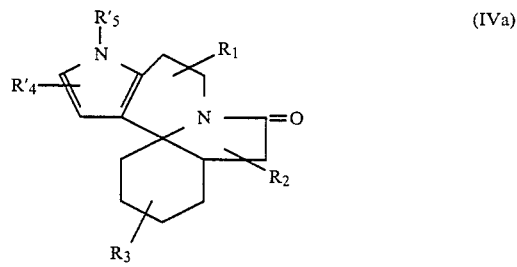
(IVa)

wherein $R_1$–$R_3$, $R'_4$ and $R'_5$ represent hydrogen or lower alkyl.

Preferred embodiments thereof relate to the compounds of formula IVa wherein $R_1$–$R_3$ and $R'_4$ represent hydrogen and $R'_5$ represents hydrogen or lower alkyl; and further to above-cited compounds of formula IVa wherein the cyclohexane and pyrrolidone rings are cis fused.

Also preferred are the octahydro-2H,8H-imidazo-[4',5':3,4]pyrido-[2,1-i]indol-2-ones of formula V

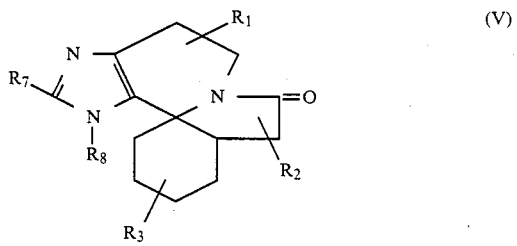
(V)

wherein $R_1$–$R_3$, $R_7$ and $R_8$ represent hydrogen or lower alkyl; and pharmaceutically acceptable acid addition salts thereof.

Preferred embodiments thereof relate to the compounds of formula V wherein $R_1$–$R_3$ and $R_7$ represent hydrogen and $R_8$ represents hydrogen or lower alkyl; and further to the above-cited compounds of formula V wherein the cyclohexane and pyrrolidone rings are cis fused; and pharmaceutically acceptable acid addition salts thereof.

A lower alkyl group within the scope of the invention may contain 1 to 7 carbon atoms, preferably 1 to 4 carbon atoms, and represents advantageously methyl.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention are useful in mammals as nootropic agents for treating cerebral insufficiency, e.g. for improving memory and learning in conditions of cognitive dysfunction and are active in state of the art test systems indicative of such activity, e.g. as described in "Techniques and Basic Experiments for the Study of Brain and Behavior", Elsevier (Publisher), 1983.

The above-cited properties are demonstrable in tests using advantageously mammals, e.g. mice, rats, cats or monkeys. Said compounds can be applied in vivo either enterally or parenterally, advantageously orally, intraperitoneally or intravenously, e.g. within gelatin capsules, as aqueous suspensions or in aqueous solutions. The dosage may range between about 0.01 and 300 mg/kg, preferably between about 0.05 and 100 mg/Kg, advantageously between about 0.1 and 50 mg/Kg.

The above-cited properties can be determined, for instance, in the electroshock induced amnesia test in mice, e.g. described by Mondadori et al in Acta Neurol. Scand. 69, Suppl. 99, 125–129 (1984), in the step-down passive avoidance test in mice and rats, e.g. described by Mondadori in Psycholpharmacol. 63, 297–300 (1979) and Neuropharmacology 7, Suppl. 3, 27–38 (1986), and in the active avoidance test in aged rats.

The test to measure the inhibition of electro-shock-induced amnesia in mice is carried out as follows:

The apparatus consists of a large box ($35 \times 20 \times 10$ cm) which is connected by means of a sliding door to a small box ($10 \times 10 \times 18$ cm). The small box is brightly lit from above by a 100 watt lamp, whereas the large box is dark. The floor of both compartments consists of an electrified grating, the rods of which (diameter: 6 mm) are each spaced 13 mm apart.

For treatment, male mice having a body weight of 20–22 g are placed into the brightly lit small box. As mice have an instinctive preference for the dark, they usually go into the dark compartment within 30 seconds. As soon as all the mice have entered this compartment, the sliding door is closed and a shock (1 mA, 5 seconds) is administered to the paws of the mice. The animals are then immediately taken out of the testing unit. Two separate assays are carried out (in the morning between 8 and 11 a.m. and in the afternoon between 12 noon and 3 p.m.)

To test their learning performance, the mice are once more placed individually into the lit compartment and the time until the are all in the dark (the step-through latency) is measured. Most of the animals will now normally remain in the lit compartment over the entire observation time of 150 seconds.

The memory of the shock applied to the paws is at least partially eliminated if an amnesia-inducing treatment, consisting of a brief electroshock treatment, is administered directly after the shock to the paws is applied in the training session. Parameters of the electroshock: 50 mA, 0.4 sec., 50 Hz.

To determine the protective action against the amnesia-inducing action of the electroshock, the animals are divided into different groups and the test compound is administered intraperitoneally 30 minutes before the training procedure, with vehicle alone (=placebo) being administered to control groups. The animals are subjected to electroshock treatment immediately after training. The degree of the learning performance still retained is measured 24 hours later from the residence time in the lit box (step-through latency period) compared with that obtained with control animals to which vehicle only has been administered.

Prolongation of the step-through latency period in the electroshock treated animals is indicative of enhancement of retention performance by the test compound.

Illustrative of the invention, the compound of example 1 prolongs the step-through latency in the electroshock-induced amnesia model (inhibits electroshock-induced amnesia) at a dose of e.g. 3 mg/Kg i.p. in mice.

The step-down passive avoidance test to measure the enhancement of learning and memory (of retention performance) in mice is carried out as follows:

The apparatus consists of an electrified grid ($50 \times 50$ cm) of stainless steel rods (4 mm in diameter, 13 mm distance between bars), enclosed by grey PVC walls 50 cm in height. In the middle of the grid is a wooden platform 12 mm high and 67 mm in diameter, which is enclosed by a removable grey PVC tube (18 cm high, 68 mm inner diameter).

Male mice (20–22 g) are placed one by one on the platform inside the tube, which is removed after 10 seconds. With a few exceptions the mice step-down from the platform within 20 seconds to explore. As soon as the animal has all four feet on the grid, it receives a footshock (1 mA, 1 sec) and is then immediately removed from the apparatus. The latency period until the animal descends is measured (baseline latency).

Twenty-four hours after the training, each animal is again placed on the platform and the "step-down latency" is recorded (retest latency) up to a cut-off time of 150 sec. Any prolongation of the retest step-down latency in comparison to the baseline is rated as a sign of learning.

The test compounds are administered to groups of 25 mice for each dose 30 minutes (i.p.) or 60 minutes (p.o.) before the training session or immediately after the shock is applied. The degree of enhancement of learning and memory is assessed 24 hours later by measuring the step-down latency period. Any increase in the latency period compared to control is indicative of the enhancement in retention performance by the test compound.

Illustrative of the invention, the compound of example 1 significantly improves performance in the step-down passive avoidance test in mice at a dose of e.g. 1 mg/Kg i.p. administered 30 minutes prior to the training session.

The effect on age-related cognitive dysfunction is determined in aged rats as follows:

Groups of rats (age 27 months at the beginning of the experiment) are treated daily p.o. with various doses of test compound or vehicle. Sixty minutes later they are subjected to a learning session in a one-way active avoidance task. A second learning session is repeated about 4 hours later.

The apparatus consists of two identical compartments measuring $20 \times 20 \times 30$ cm with electified grid floors and a connecting door ($12 \times 16$ cm).

The training session consists in placing an animal into compartment A. After a delay of 10 seconds a footshock current is turned on. By moving into compartment B the animals can either escape or avoid the footshock. Active avoidance training is continued until the animals meet the criterion of 5 consecutive avoidances. A reduction in the number of training sessions required is indicative of a facilitation in learning the active avoidance task.

Illustrative of the invention, the compound of example 1 at a dose of 10 mg/kg p.o. reduces the number of training sessions required for aged rats to learn the active avoidance task.

The aforementioned advantageous properties render the compounds of the invention useful for improving cognitive performance and for the treatment cognitive dysfunction in mammals including man, particularly for the treatment of conditions of impaired memory and learning, e.g. in senile dementia, Alzheimer's disease and dyslexia.

The compounds of the invention are prepared by processes comprising:

(a) cyclizing a compound of the formula

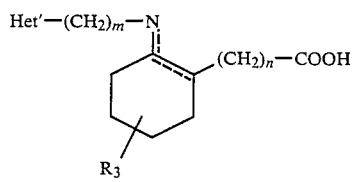

or a reactive ester derivative thereof wherein Het' represents a pyrrolyl or imidazolyl radical optionally substituted by one or two alkyl groups; m, n and $R_3$ have meaning as defined above and the chains $(CH_2)_m$ and $(CH_2)_n$ are optionally substituted by lower alkyl; or (b) cyclizing a compound of the formula

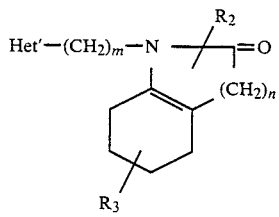

wherein Het', m, n, $R_2$ and $R_3$ have meaning as defined hereinabove;

(c) cyclizing a compound of the formula

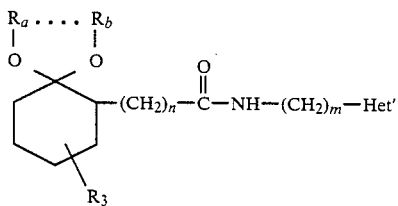

wherein $R_a$ and $R_b$ represent lower alkyl or $R_a$ and $R_b$ combined represent lower alkylene; $R_3$, Het', m and n have meaning as defined hereinabove, and wherein the $(CH_2)_n$ and $(CH_2)_m$ chains are optionally substituted by lower alkyl, by treatment with an acid; or (d) condensing a compound of the formula

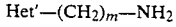 (IX)

wherein Het' and m have meaning as defined hereinabove, and wherein the $(CH_2)_m$ chain is optionally substituted by lower alkyl, with a compound of the formula

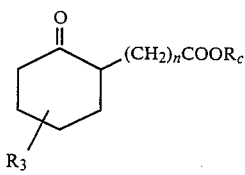

wherein $R_3$ and n have meaning as defined hereinabove, and wherein the chain $(CH_2)_n$ is optionally substituted by lower alkyl; $R_c$ represents hydrogen or lower alkyl; and treating the resulting product in situ with an anhydrous acid; or (e) reducing the ketone functional group in a compound of formula XI

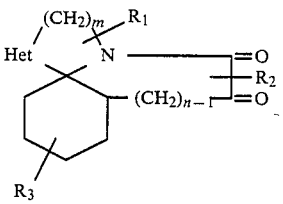

wherein Het, m, n, $R_1$, $R_2$ and $R_3$ have meaning as defined hereinabove; or (f) saturating the double bond in a compound of the formula

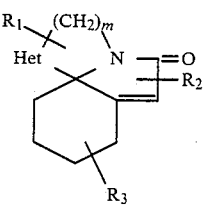

wherein Het, m, $R_1$, $R_2$ and $R_3$ have meaning as defined hereinabove, to obtain a compound of formula II.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into the free compound or into another salt; and/or a mixture of isomers or racemates obtained is separated into the single isomers or racemates; and/or, if desired, a racemate is resolved into the optical antipodes.

In starting compounds and intermediates which are converted to the compounds of the invention in a manner described herein, functional groups present, such as carboxy, amino (including ring NH) and hydroxy groups, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy, hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

Suitable protecting groups for the imidazolyl ring nitrogen include trilower alkylsilyl e.g. trimethylsilyl, lower alkanoyl e.g. acetyl, dilower alkylcarbamoyl e.g. dimethylcarbamoyl, or triarylmethyl e.g. triphenylmethyl.

As referred to in the context of the application reactive ester derivatives of carboxylic acids include those generally known in the art, particularly lower alkyl esters and cyanomethyl esters.

A reactive esterified hydroxy group as mentioned herein represents a leaving group, particularly hydroxy esterified by a strong acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

The cyclization under process (a) is carried out optionally in the presence of an anhydrous acid such as glacial acetic acid or polyphosphoric acid in an inert solvent such as ethanol, toluene or xylene, preferably at an elevated temperature ranging from about 60° to 175°.

The starting materials of formula VI are prepared preferably in situ, e.g. by condensation of a compound of formula IX as defined above with a compound of formula X as defined above, preferably wherein Rc represents lower alkyl, in an inert solvent, such as toluene, with simultaneous removal of water.

The cyclization according to process (b) is carried out essentially as described under process (a).

The starting materials of formula VII can be preferably prepared in situ by heating e.g. a lower alkyl ester of a compound of formula VI in an inert solvent such as toluene.

The starting materials of formula VII can also be prepared by condensing a compound of the formula XIII Het'—(CH$_2$)$_m$—X  (XIII)

wherein Het' and m have meaning as defined hereinabove, the (CH$_2$)$_m$ chain is optionally substituted by lower alkyl and X represents reactive esterified hydroxy, such as halo, with a compound of the formula XIV

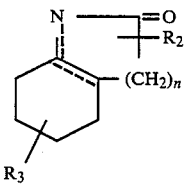

wherein R$_2$, R$_3$ and n have meaning as defined hereinabove.

The starting materials of formula XIV can be prepared in situ by e.g. condensing an ester of formula X above with ammonia or a salt thereof and removing the water generated during the condensation e.g. by azeotropic distillation.

The cyclization according to process (c) can be carried out by treatment of a compound of formula VIII with an acid, e.g. phosphoric acid or polyphosphoric acid in toluene at elevated temperature.

The starting materials of formula VIII can in turn be prepared by condensation of e.g. an acid of formula XV

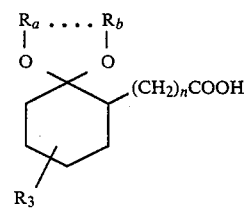

wherein R$_a$ and R$_b$ represent lower alkyl or R$_a$ and R$_b$ combined represent lower alkylene; R$_3$ and n have meaning as defined above and wherein the (CH$_2$)$_n$ chain is optionally substituted by lower alkyl, with an amine of formula IX above, e.g. in the presence of a condensing agent such as dicyclohexylcarbodiimide.

The preferred one step condensation according to process (d) is carried out e.g. in an inert solvent such as toluene or xylene with removal of water at or near reflux temperature, or in the presence of an acid such as acetic acid in an inert solvent such as ethanol or toluene.

The starting materials of formula IX and X are known in the art or can be prepared according to methods well-known in the art or as illustrated herein.

The reduction according to process (e) can be carried out according to procedures known in the art for selectively converting a ketone carbonyl grouping to the corresponding CH$_2$ grouping, e.g. under conditions of a Wolff-Kishner reaction.

The starting materials of formula XI can be prepared, e.g. for the compounds wherein n represents 1, by first condensing a compound of formula IX wherein Het' and m have meaning as defined above with a compound of formula X wherein n is zero and R$_c$ represents lower alkyl, under conditions described in process (d) to obtain a compound of formula XVI which is condensed with oxalyl chloride to obtain a compound of formula XVII

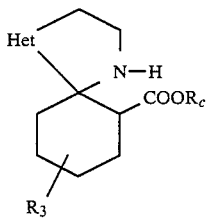

(XVI)

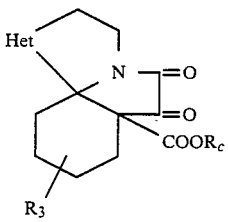

(XVII)

wherein Het and $R_3$ have meaning as defined hereinabove and $R_c$ is lower alkyl. Conversion to the decarboxylated product of formula XI, wherein n represents the integer 1, can be carried out e.g. by treatment with magnesium chloride in dimethylsulfoxide.

The reduction according to process (f) can be carried out according to procedures well-known in the art for reduction of a double bond, e.g. using hydrogenation with hydrogen in the presence of a suitable catalyst, such as platinum, in a suitable solvent such as acetic acid.

The starting materials of formula XII can be prepared, e.g. from compounds of formula XI hereinabove wherein n represents the integer 1, by selective reduction of the ketone functional grouping to the corresponding alcohol e.g. by catalytic hydrogenation or with a selective reducing agent such as sodium borohydride, treating the resulting alcohol with e.g. tosyl chloride in pyridine and heating said derivative, e.g. in collidine at elevated temperature.

The compounds of the invention, e.g. of formula I wherein Het represents bonded pyrrole or imidazole as represented by (a), (c), (d) or (e) hereinabove in which $R_5$, $R_8$, $R_9$ or $R_{11}$, respectively, represent hydrogen, can be converted to the respective compounds wherein $R_5$, $R_8$, $R_9$ or $R_{11}$ represent lower alkyl according to N-alkylation methods well-known in the art, by condensation with a reactive derivative of the corresponding lower alkyl alcohol, e.g. a halide such as the bromo or iodo derivative in the presence of an anhydrous base such as an alkali metal hydride (e.g. sodium or potassium hydride), an alkoxide (e.g. sodium methoxide or ethoxide, potassium tert-butoxide) or an alkali metal amide (e.g. lithium diisopropylamide) using an inert solvent such as dimethylformamide or tetrahydrofuran.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, as racemates or as mixtures of diastereomeric racemates including cis and trans ring fused isomers. The aforesaid possible isomers or mixtures thereof are within the purview of this invention.

Any mixtures of isomers can be separated on the basis of the physico-chemical differences of the constituents, in known manner, into the pure isomers for example by chromatography and/or fractional crystallization.

Resulting racemates can be resolved into the optical antipodes by known methods, including chiral chromatography. Racemic basic products of the invention (those containing an imidazole ring) can be resolved into their optical antipodes, e.g., by the fractional crystallization of d- or 1-(tartrate, mandelate or camphorsulfonate) salts. Advantageously, the more active of the two antipodes is isolated.

Finally the compounds of the invention are either obtained in the free form, or a salt thereof for compounds containing an imidazole ring. Any resulting free base can be converted into a corresponding acid addition salt, preferably with the use of a therapeutically useful acid, or a resulting salt can be converted into the corresponding fee base, for example, with the use of a stronger base, such as a metal or ammonium hydroxide or a basic salt, e.g. an alkali metal hydroxide or carbonate, or a cation exchange preparation, or an alkylene oxide such as propylene oxide. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, e.g. for the treatment of disorders involving cognitive dysfunction, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The invention also relates to a method of improving cognitive performance and of treating cognitive disorders (conditions of cognitive dysfunction) in mammals, particularly conditions of impaired memory and learning, such as senile dementia and Alzheimer's disease, comprising the administration to a mammal in need thereof of an effective cognition (learning and memory) enhancing amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR).

EXAMPLE 1

A solution of 41.2 g of 2-(1-pyrrolyl)-ethylamine, 69 g of ethyl cyclohexanone-2-acetate in 900 ml toluene is stirred and refluxed for 16 hours using a Dean Stark water separator. The reaction is cooled and 100 ml glacial acetic acid is added. The solution is stirred and refluxed as before for 6 hours, cooled and the organic solvents are evaporated under reduced pressure. The residue is dissolved in methylene chloride and washed with ice cold 1N aqueous sodium hydroxide. The organic layer is separated, dried over magnesium sulfate, treated with 10 g decolorizing charcoal and filtered. The methylene chloride solution is evaporated under reduced pressure and the residue is crystallized from ether by cooling to 5° to give (9b,13a-cis)-2H-1,4,5,10,11,12,13,13a-octahydropyrrolo[2',1':3,4]-pyrazino[2,1-i]indol-2-one, m.p. 102°–104°, the compound of formula III wherein $R_1$, $R_2$, $R_3$ and $R_6$ represent hydrogen and wherein the 9b,13a-ring junction is cis.

The starting material, 2-(1-pyrrolyl)-ethylamine, is prepared as follows:

A solution of 140 g of ethylenediamine and 300 g of 2,5-dimethoxytetrahydrofuran in 2000 ml of dioxane and 1700 ml of glacial acetic acid is stirred and refluxed for 6 hours. The reaction mixture is then cooled and the solvents evaporated under reduced pressure at 60°. The dark residue is taken up in methylene chloride and ice and basified with 3N aqueous sodium hydroxide. The organic layer is separated and extracted into 5 N aqueous hydrochloric acid. The acid extract is made basic with cooling and is extracted with methylene chloride. The organic phase is dried over magnesium sulfate, treated with 10 g of charcoal and filtered. The methylene chloride is evaporated under reduced pressure to give an N-acetyl-2-(1-pyrrolyl)-ethylamine as an oil.

A mixture of 220 g of N-acetyl-2-(1-pyrrolyl)-ethylamine as obtained above and 1800 ml of 10% aqueous sodium hydroxide is heated under reflux for 16 hours, cooled and then extracted with 2500 ml of methylene chloride. The organic layer is separated, dried over magnesium sulfate, treated with 20 g of charcoal and filtered. The filtrate is evaporated under reduced pressure to give an oil which is distilled under high vacuum at 0.2 mm Hg to give 2-(1-pyrrolyl)-ethylamine as a clear oil.

EXAMPLE 2

(a) Similarly prepared according to procedure given in Example 1 is the compound of formula I wherein $R_1$, $R_2$ and $R_3$ represent hydrogen, n represents the integer 1, m represents the integer 3 and Het represents

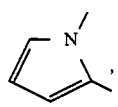

and wherein the cyclohexane and pyrrolidone rings are cis fused, m.p. 78°–79°, starting with 1,3-diaminopropane so as to obtain 3-(1-pyrrolyl)-propylamine which is then condensed with ethyl cyclohexanone-2-acetate.

(b) Similarly prepared according to procedure given in Example 1 is the compound of formula I wherein $R_1$, $R_2$ and $R_3$ represent hydrogen, n represent the integer 2, m represents the integer 2 and Het represents

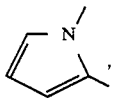

by condensation of ethyl cyclohexanone-2-propionate with 2-(1-pyrrolyl)-ethylamine.

EXAMPLE 3

A solution of 3.3 g of 2-(3-pyrrolyl)-ethylamine, 5.5 g of ethyl cyclohexanone-2-acetate and 150 ml of toluene is stirred and heated under reflux for 7 hours. The reaction mixture is cooled to room temperature and stirred overnight to crystallize the cis fused compound of formula IV wherein $R_1$–$R_5$ represent hydrogen, namely (cis)-1,4,5,9,10,11,12,12a-octa-hydro-2H-pyrrolo[2',3':3,4]pyrido[2,1-i]indol-2-one, m.p. 197°–199°.

EXAMPLE 4

To a solution of 4.0 g of the compound of example 3, (the compound of formula IV wherein $R_1$–$R_5$ represent hydrogen) in 60 ml of dimethylformamide is added in portions 1.0 g of 50% of sodium hydride in mineral oil which was first washed free of mineral oil. The reaction mixture is stirred at room temperature for 1½ hours and then cooled. Methyl iodide (3.0 ml) is added, the reaction mixture is stirred at room temperature overnight and then poured into ice-water. The mixture is extracted with ether, the ether extract is washed with brine, dried and evaporated to dryness. The residue is crystallized from ether to yield the cis fused compound of formula IV wherein $R_1$–$R_4$ represent hydrogen and $R_5$ represents methyl, namely (cis)-8-methyl-1,4,5,9,10,11,12,12a-octahydro-2H-pyrrolo[2',3':3,4]pyrido[2,1-i]indol-2-one, m.p. 100°–102°.

EXAMPLE 5

Similarly prepared according to the procedures given in the previous examples are:

(a) (cis)-1,4,5,9,10,11,12,12a-octahydro-2H-pyrrolo[3',2':3,4]pyrido[2,1-i]indol-2-one, m.p. 181°–183°, the cis fused compound of formula IVa wherein $R_1$–$R_3$, $R'_4$ and $R'_5$ represent hydrogen, starting with 2-(2-pyrrolyl)-ethylamine;

(b) (cis)-6-methyl-1,4,5,9,10,11,12,12a-octahydro-2H-pyrrolo[3',2':3,4]pyrido[2,1-i]indol-2-one, m.p. 93°–95°, the cis fused compound of formula IVa wherein $R_1$–$R_3$ and $R'_4$ represent hydrogen, and $R'_5$ represents methyl, starting with 2-(2-pyrrolyl)-ethylamine.

EXAMPLE 6

To 1.9 g of histamine dihydrochloride is added approximately 2 g of triethylamine, the mixture is stirred at room temperature for 30 minutes and the excess triethylamine removed by evaporation under reduced pressure. The residue is dissolved in 50 ml ethanol, and 1.9 g of ethyl cyclohexanone-2-acetate and 5 ml of acetic acid are added. The reaction mixture is heated at reflux temperature overnight and the solvent removed by evaporation under reduced pressure. The residue is then washed with 200 ml ether and basified to pH 9 with 10% ammonium hydroxide solution. The reaction mixture is then extracted with 2×150 ml of methylene chloride. The methylene chloride extracts are combined, dried over anhydrous sodium sulfate, and the solvent removed by evaporation under reduced pressure to yield a residue which is then purified chromatographically to yield (cis)-1,4,5,9,10,11,12,12a-octahydro-2H,8H-imidazo[4',5':3,4]pyrido[2,1-i]indol-2-one, m.p. 167°–169°, the cis fused compound of formula V wherein $R_1$–$R_3$, $R_7$ and $R_8$ represent hydrogen.

EXAMPLE 7

A mixture of 2.75 g of 2-(1-pyrrolyl)-ethylamine, 5.1 g of ethyl cyclohexanone-2-acetate, 4 ml of glacial acetic acid and 50 ml of ethanol is heated under reflux overnight. The reaction mixture is evaporated to dryness and the residue is neutralized with 10% ammonium hydroxide solution. The mixture is extracted with methylene chloride, the extract is washed with saturated sodium bicarbonate solution and evaporated to dryness. The residue is separated by thin layer chromatography to yield the trans fused (9b,13a-trans)-2H-1,4,5,10,11,12,13,13a-octahydropyrrolo[2',1':3,4-]pyrazino[2,1-i]indol-2-one, m.p. 69°–71°, and the corresponding cis fused compound of example 1.

EXAMPLE 8

(a) Preparation of 10,000 tablets each containing 25 mg of the active ingredient:

| Formula: | |
| --- | --- |
| (9b,13a-cis)-2H—1,4,5,10,11,12,13,13a-octahydropyrrolo[2',1':3,4]pyrazino-[2,1-i]indol-2-one | 250.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

Procedure:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(b) Preparation of 1,000 capsules each containing 10 mg of the active ingredient:

| Formula: | |
| --- | --- |
| (9b,13a-cis)-2H—1,4,5,10,11,12,13,13a-octahydro-pyrrolo[2',1':3,4]pyrazino-[2,1-i]indol-2-one | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A compound of the formula

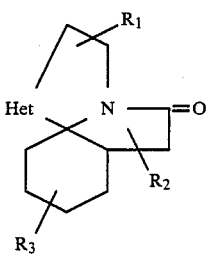 (II)

wherein $R_1$, $R_2$ and $R_3$ independently represent hydrogen or lower alkyl; Het represents

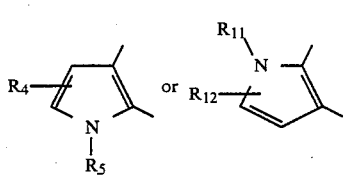

wherein $R_4$, $R_5$, $R_{11}$ and $R_{12}$ independently represent hydrogen or lower alkyl.

2. A compound according to claim 1 of the formula

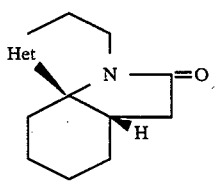 (IIa)

wherein Het represents

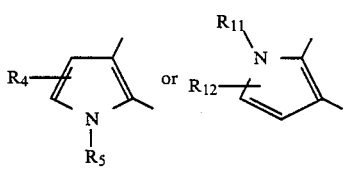

wherein $R_4$, $R_5$, $R_{11}$ and $R_{12}$ independently represent hydrogen or lower alkyl.

3. A compound according to claim 1 of the formula IV

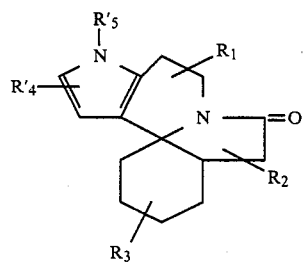 (IV)

wherein $R_1$–$R_5$ represent hydrogen or lower alkyl.

4. A compound according to claim 3 wherein $R_1$–$R_4$ represent hydrogen, $R_5$ represents methyl, and wherein the cyclohexane and pyrrolidone rings are cis fused.

5. A compound according to claim 1 of the formula IVa

 (IVa)

wherein $R_1$–$R_3$, $R'_4$ and $R'_5$ represent hydrogen or lower alkyl.

6. A pharmaceutical composition suitable for the treatment of impaired memory and learning in mammals comprising an effective learning and memory enhancing amount of a compound according to claim 1 in combination with one or more pharmaceutical acceptable carriers.

7. A pharmaceutical composition suitable for the treatment of impaired memory and learning in mammals comprising an effective learning and memory enhancing amount of a compound of claim 4 in combination with one or more pharmaceutically acceptable carriers.

8. A method of treating conditions of impaired memory and learning in a mammal which comprises administering to a mammal in need thereof an effective memory and learning enhancing amount of a compound of claim 1 or of said compound in combination with one or more pharmaceutically acceptable carriers.

9. A method of treating conditions of impaired memory and learning in a mammal which comprises administering to a mammal in need thereof an effective memory and learning enhancing amount of a compound of claim 4 of a said compound in combination with one or more pharmaceutically acceptable carriers.

* * * * *